(12) United States Patent
Boulange et al.

(10) Patent No.: US 9,611,311 B2
(45) Date of Patent: Apr. 4, 2017

(54) ALBUMIN-PURIFICATION METHOD COMPRISING A NANOFILTRATION STEP, SOLUTION, AND COMPOSITION FOR THERAPEUTIC USE CONTAINING THE SAME

(71) Applicant: LABORATOIRE FRANCAIS DU FRACTIONNEMENT ET DES BIOTECHNOLOGIES, Les Ulis (FR)

(72) Inventors: Paul Boulange, Orsay (FR); Sami Chtourou, Elancourt (FR); Stephane Boyer, Pecqueuse (FR); Roland Schmitthaeusler, Montigny le Bretonneux (FR); Bruno Padrazzi, Paris (FR)

(73) Assignee: LABRATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

(21) Appl. No.: 14/611,460

(22) Filed: Feb. 2, 2015

(65) Prior Publication Data

US 2015/0152162 A1 Jun. 4, 2015

Related U.S. Application Data

(63) Continuation of application No. 10/589,825, filed as application No. PCT/FR2005/000416 on Feb. 23, 2005, now abandoned.

(30) Foreign Application Priority Data

Feb. 27, 2004 (FR) ...................................... 04 02001

(51) Int. Cl.
| | |
|---|---|
| *C07K 1/34* | (2006.01) |
| *C07K 14/76* | (2006.01) |
| *C07K 14/765* | (2006.01) |
| *C07K 14/755* | (2006.01) |
| *A61K 38/00* | (2006.01) |

(52) U.S. Cl.
CPC ................ *C07K 14/76* (2013.01); *C07K 1/34* (2013.01); *C07K 14/755* (2013.01); *C07K 14/765* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,346,992 | A | 9/1994 | Grandgeorge et al. |
| 6,150,504 | A | 11/2000 | Van Der Laken et al. |
| 6,210,683 | B1 | 4/2001 | Burke et al. |
| 6,399,357 | B1 | 6/2002 | Winge |
| 6,806,355 | B2 | 10/2004 | Joergensen et al. |
| 2003/0232969 | A1 | 12/2003 | Lengsfeld et al. |

FOREIGN PATENT DOCUMENTS

| | | |
|---|---|---|
| EP | 0498133 A1 | 8/1992 |
| EP | 0570916 A2 | 11/1993 |
| EP | 1329460 A1 | 7/2003 |
| EP | 1329461 A1 | 7/2003 |
| EP | 1614424 A1 | 1/2006 |
| WO | WO 92/04367 A1 | 3/1992 |
| WO | WO 96/00237 A1 | 1/1996 |

OTHER PUBLICATIONS

Asahi Kasei Medical, "Planova Filters for virus removal", Virus Removal for Biotherapeutic Products, cited in Parent Application Mar. 17, 2010, Internet excerpt, 3 Pages.
Burnouf et al., "Properties of a Highly Purified Human Plasma Factor IX: c Therapeutic Concentrate Prepared by Conventional Chromatography", Vox Sang, vol. 57, No. 4, 1989, pp. 225-232.
Burnouf et al., "Reducing the risk of infection from plasma products: specific preventative strategies", Blood Reviews, vol. 14, 2000, pp. 94-110.
Burnouf-Radosevich et al., "A therapeutic, highly purified factor XI concentrate from human plasma", Transfusion, vol. 32, No. 9, Nov.-Dec. 1992, pp. 861-867.
Burnouf-Radosevich et al., "Nanofiltration, a New Specific Virus Elimination Method Applied to High-Purity Factor IX and Factor XI Concentrates", Vox Sang, vol. 67, No. 2, 1994, pp. 132-138.
Cohn et al., "Preparation and Properties of Serum and Plasma Proteins. IV. A System for the Separation into Fractions of the Protein and Lipoprotein Components of Biological Tissues and Fluids", Separation into Fractions of Protein and Lipoprotein Components, vol. 8, Mar. 1946, pp. 459-475.
Créange et al., "Creutzfeldt-Jakob Disease after Liver Transplantation", Annals of Neurology, vol. 38, No. 2, Aug. 1995, pp. 269-272.
Falbe et al., "Rompp Chemie Lexikon", 9th Edition, publisher Georg Thieme Verlag Stuttgart-New York, vol. 3, 2 Pages.
Jacobs et al., "Ultrafilter Membranes in Biochemistry", Methods of Biochemical Analysis, vol. 22, 1974, pp. 307-354.
Kasper et al., "Registry of Clotting Factor Concentrates", World Federation of Hemophilia, fifth Edition, 2004, No. 6, Jan. 2004, 14 Pages.
Kistler et al., "Large Scale Production of Human Plasma Fractions: Eight Years Experience with the Alcohol Fractionation Procedure of Nitschmann, Kistler and Lergier", Vox Sang, vol. 7, No. 4, Jul.-Aug. 1962, pp. 414-424.

(Continued)

*Primary Examiner* — Anand Desai
(74) *Attorney, Agent, or Firm* — Birch, Stewart, Kolasch & Birch, LLP

(57) ABSTRACT

The invention relates to an albumin-purification method comprising a step consisting in subjecting an aqueous albumin solution, with a concentration of between 15 g/l and 80 g/l and a pH of not lass than 7, to nanofiltration in a temperature range of between 15 DEG C and 55 DEG C. The invention also relates to: a virally-safe aqueous albumin solution which can be obtained using the inventive method and in which the sites for the transport and binding of the active therapeutic ingredients of the albumin are available; and an albumin composition for therapeutic use, which is obtained by adapting the albumin solution that is intended for clinical use.

13 Claims, 6 Drawing Sheets

(56) References Cited

OTHER PUBLICATIONS

Mehta et al., "Purifying Therapeutic Monoclonal Antibodies", Society for Biological Engineering, CEP, vol. 104, No. 5, 2008, pp. S14-S20.
Morgenthaler, "Securing Viral Safety for Plasma Derivatives", Transfusion Medicine Reviews, vol. 15, No. 3, Jul. 2001, pp. 224-233.
Pharmacopée Européenne, "Albumine Humaine (Solution D')", Chapitre, 4éme Edition, Jan. 2010, p. 642, (4 Pages total).
Tarelli et al., "Recombinant Human Albumin as a Stabilizer for Biological Materials and for the Preparation of International Reference Reagents", Biologicals, vol. 26, 1998, pp. 331-346.
Tateishi et al., "Scrapie Removal Using Planova Virus Removal Filters", Biologicals, vol. 29, 2001, pp. 17-25.
Wallis et al., "Concentration of Viruses From Water by Membrane Chromatography", Ann. Rev. Microbiol., vol. 33, 1979, pp. 413-437.

ALBUMIN-PURIFICATION METHOD COMPRISING A NANOFILTRATION STEP, SOLUTION, AND COMPOSITION FOR THERAPEUTIC USE CONTAINING THE SAME

CROSS REFERENCE TO RELATED APPLICATIONS

This application is a Continuation of copending application Ser. No. 10/589,825, filed on Dec. 15, 2006, which was filed as PCI International Application No. PCT/FR05/000416 on Feb. 23, 2005, which claims the benefit under 35 USC. § 119(a) to patent application Ser. No. 0402001, filed in FRANCE on Feb. 27, 2004, all of which are hereby expressly incorporated by reference into the present application.

FIELD OF THE INVENTION

The present invention relates to an albumin purification method comprising a nanofiltration step, a solution and a composition for therapeutic use containing the same, obtainable by the method of the invention.

BACKGROUND OF THE INVENTION

Albumin is a major protein of human or animal blood plasma. Clinical use of albumin, as an active ingredient, requires its extraction and purification, which is traditionally carried out by known methods, such as those of Cohn et al. (J. Am. Chem. Soc., 68, 459, 1946) and Kistler et al. (Vox Sang., 7, 1962, 414-424) which are additionally applicable to an industrial scale.

Albumin requirements amount to about 100-300 kg per million inhabitants according to country; for that reason, it is necessary, for clinical purposes, to provide an albumin free from pathogenic viruses and contaminants, which are sources of diseases. Thus, as regards transfusion-transmissible viruses, safety is ensured by viral inactivation methods such as liquid-state pasteurisation of an albumin composition at 60° C. for 10 hours in the presence of a biologically compatible stabiliser (sodium caprylate and/or tryptophanate). This viral safety has been established for more than 60 years and the literature does not report any proven case of virus transmission, e.g. hepatitis B, A or C, or HIV. However, some authors mentioned some cases correlated with the presence, after transfusions, of parvoviruses B 19 in albumin compositions or albumin derivate products. Furthermore, a case has also been reported of an albumin composition that would have led to Creutzfeldt-Jakob disease in a patient having undergone liver transplantation (Créange A., 1995).

Some studies revealed a series of adverse effects occurring after an albumin transfusion due to the presence of lipopolysaccharide substances (pyrogens) in amounts lower than the detection threshold of authorised methods, but capable of occurring during perfusions with large volumes of albumin (e.g. plasma exchanges).

Other side effects are related to the presence of albumin polymers occurring during albumin purification and especially during the above-mentioned pasteurisation step. Others are related to the presence of added stabilisers to prevent the thermal denaturation linked to pasteurisation, especially in patients with allergic backgrounds.

In order to avoid the risk of transmissible infectious agents being present, it has been suggested to produce a so-called "recombinant" albumin, according to U.S. Pat. No. 6,210,683: the gene of albumin is introduced into a host cell, yeast or bacterium, having a high proliferation potential. In turn, this host cell produces albumin in the culture medium or its cytoplasm. This albumin is then separated from the cells by extraction and purified. However, the presence of host cell proteins is often detected and the purification methods must therefore have a very high resolution, which is generally detrimental to the yield. The production cost of a recombinant albumin may then prove to be too high in comparison to that of an albumin generated from plasma.

Another possibility to get round the above-mentioned drawbacks is to implement filtration methods extensively used for the retention of viruses, and chemical or bacteriological contaminants, etc., using qualified filters with variable porosities. One can mention for instance ultrafiltration that has been used from time to time in the absence of other means of virus elimination to ensure the biological safety of an extraction protein such as growth hormone (hGH). The method requires a tangential flow and is only intended for protein solutions or polypeptides having molecular weights equal to or lower than 65 kDa and low concentrations. This leaves chance for viruses to pass through due to the manufacturing imprecision of filtration membranes. Moreover, filter clogging occurs in front operation, resulting in a blockage of the filtrate flow. Filter clogging is all the faster as protein or polypeptide concentration increases.

To increase the viral safety of biological solutions further, it is contemplated to implement nanofiltration, the preferred method for the retention of particles with sizes equal to or greater than about 15-20 nm. This particle retention on qualified filters is easily achieved on a large scale with aqueous solutions or solutions containing small-sized solutes, peptides, amino-acids, mineral ions or organic compounds smaller than about 5 kDa.

The nanofiltration of large-sized solutes has been achieved, fox example, with blood coagulation factors, factor IX and factor XI. The article by Burnouf-Radosevich et al. (Vox Sang., 67, p. 132-138, 1994 in reference with Burnouf et al., Vox Sang., 57, p. 225-232, 1989 and Burnouf-Radosevich et al., Transfusion, 22, p. 861-867, 1992) shows that the working conditions of the nanofiltration method imply small volumes of factor IX and factor XI concentrates (3-4 litres), with protein concentrations not exceeding 1 g/L (0.21 g/L and 0.75 g/L, respectively).

Actually, during the nanofiltration process, the large-sized solutes accumulate on the filter, which slows down the filtrate flow until the filter is completely clogged.

The technical solutions to this clogging which consist of implementing a tangential flow nanofiltration, increasing the pressure and changing the directions of the flows do not prove to be efficient because the clogging is progressive and irreversible. An industrial development is therefore greatly compromised because it requires the use of very numerous filters and very large volumes of solutions to be filtered, which generates a prohibitive cost and abnormally increased manufacturing times.

To avoid the clogging phenomenon, a solution consists of adjusting the physicochemical parameters influencing the recovery yield of solutes, while avoiding the passage of contaminants through the filter. Varying these parameters—such as ionic strength, the nature of the solute to be filtered and the pH of the solution to be filtered—as well as the working conditions of the filtration—such as flow rate and pressure—has been the subject of many studies. For instance, the scientific publications by C. Wallis et al., Ann. Rev. Microbiol., 33, p. 413-437, 1979 and S. Jacob, Methods of Biochemical Analysis, 22, p. 307-350, 1974, show that the effect of each parameter can individually result in increased or decreased efficiency of virus retention and recovery yield of solutes, and that combining several parameters does not systematically favour a synergy of the effects of improvement of the filtration conditions.

SUMMARY OF THE INVENTION

Considering the clinical significance of albumin and the ever-increasing needs in albumin, it appears necessary to supply patients with an albumin showing degrees of safety and tolerance higher than those of the currently available albumins, while optimising the conditions of a large-scale production. For that purpose, the Applicant therefore strived to develop an albumin purification method comprising a step of nanofiltering concentrated albumin solutions satisfying these objectives. Therefore, the object of the present invention is to provide a solution corresponding to a good compromise between two criteria, the retention efficiency of viruses and/or other macromolecules likely to induce diseases or side effects in patients, and the recovery yield of albumin, the relative importance of these two criteria depending on the desired application.

Accordingly, the invention relates to a method for purifying albumin comprising a step of submitting an aqueous solution of albumin, with a concentration of 15 g/L to 80 g/L and a pH not lower than 7, to a nanofiltration in a temperature range of 15° C. to 55° C.

Thus, the Applicant surprisingly found that using a judicious combination of pH, albumin concentration and temperature (and consequently viscosity) values, in the aqueous albumin solution submitted to the nanofiltration step, makes it possible to reach an efficient optimisation of the albumin recovery yield, and rates of reduction of viruses and other undesirable macromolecules higher than the limits set by the control authorities (4 log). It has been brought to light that a nanofiltration carried out under the conditions of the invention makes it possible to filter amounts higher than 5 kg albumin per $m^2$ filter, thus defining the protein load, while optimising the duration of the operation and the filtrate flow rate. The nanofiltered albumin solutions show a very high degree of safety in respect of particulate contaminants with a size of e.g. at least about 13 nm, e.g. viruses such as non-enveloped viruses, prions, albumin polymers (tetramers-decamers) generated during steps of albumin manufacture or during the pasteurisation at 60° C., micelle-like lipopolysaccharides, nucleic acids and aggregated proteins. The aqueous albumin solutions thus obtained are also an intermediate product capable of being processed into pharmaceutical formulations for clinical use (see further on).

DETAILED DESCRIPTION OF THE PREFERRED EMBODIMENTS

In the context of the invention, the aqueous albumin solutions are solutions free from any reagent employed during various classical steps of albumin manufacture or purification, such as e.g. polyethyleneglycol (PEG), ethanol, organic salts (sodium caprylate, etc.) and inorganic salts. These various reagents are removed from the albumin solution by known processes, such as diafiltration, ultrafiltration, dialysis, etc. As explained above, the presence of such reagents, or variations in their respective concentrations from one sample to another, can result in unfavourable efficiencies in terms of virus retention and albumin recovery.

Thus, surprisingly, the Applicant has further found that a decreasing ionic strength is correlated with a better viral reduction.

It should be made clear that, in the context of the invention, the aqueous albumin solutions submitted to the nanofiltration may have an ionic strength lower than a maximum threshold connected, in this case, with the maximum allowable basic pH value. This value typically corresponds to about 11.5. The pH must be controlled in particular so that the variation in ionic strength caused by the addition of a pH control agent to the aqueous albumin solution is only very small, if not insignificant. Such pH controllers will preferably be selected among strong alkali metal bases such as NaOH and KOH, and among strong acids such as HCl, while respecting the above-mentioned criteria. Furthermore, it is preferable to avoid pH controllers based on organic compounds, such as organic bases.

Thus, as an example, when aqueous albumin solutions require pH adjustment up to the value of about 11.5, which is achieve by adding 0.5 M NaOH, the solutions obtained will therefore have an ionic strength of about 0.0032.

The method of the invention may be implemented with ail types of frontal or tangential nanofiltration devices, in particular frontal nanofiltration devices, known to those skilled in the art. Currently used filters have pore sizes smaller than 100 nm.

The nanofiltration step according to the invention is preferably carried out on qualified filters having porosities of at least 13 nm, for example the nanometric filters with porosities of 15±2 or 20±2 nm which are commercially available as pleated membranes, flat membranes or hollow fibres. Regenerated cellulose nanofilters such as PLANOVA® having a porosities of 15 nm and surface areas of 0.01 $m^2$ (from Asahi, Japan), or PALL virus filters (U.S.A.) with porosities of 20 or 50 nm, may be mentioned by way of example.

Any source of albumin starting material (freeze-dried pure product, concentrate, etc.) may be used, in particular those resulting from the fractionation of human or animal blood plasma according to the methods of Conn et al. (J. Am. Chem. Soc., 68, 459, 1946) or Kistler et al. (Vox Sang., 7, 1962, 414-424).

The pH of the aqueous albumin solution is preferably in the range from about 7.8 to about 11.5, and more preferably, from 9 to 10.5. Albumin, is irreversibly altered by pH values higher than approximately 11.5.

The method of the invention is preferably implemented with aqueous albumin solutions having concentrations in the range of 40 to 60 g/L and in a temperature range of 30 to 55° C.

According to the invention, the method may further comprise a step of adding a pharmaceutically acceptable salt or salt mixture to the aqueous albumin solution to provide a solution with an ionic strength higher than 0.0032, and preferably, in the range of 0.01 to 0.55, more preferably, of 0.01 to 0.3, even more preferably, of 0.05 to 0.15, and in particular, of 0.1 to 0.13. Alkali metal salts are preferably used, in particular sodium chloride present in an amount imparting to the albumin solution an ionic strength of 0.15.

Although any albumin may be suitably used as starting material, its origin may be a factor affecting the nanofiltration yield, depending on whether it contains thermal stabilisers or was heat-treated (thermal shock or pasteurisation). Thus, in the method according to the invention, using an albumin obtained by ethanol extraction according to Cohn et al. or Kistler et al. as mentioned above, and purified by ion-exchange or affinity chromatography, can result in an increased albumin recovery and/or a reduced filtration duration.

The nanofiltration of the aqueous albumin solution can be carried out in two successive steps on two filters with decreasing porosities, respectively. Advantageously, these two successive steps are carried out on filters with porosities of 23 to 50 nm and 15 or 20 nm, respectively.

When PLANOVA® filters with porosities of 15 nm and surface areas of 0.01 m² are used, the method of the invention is implemented at pressures not exceeding 1 bar, preferably in the range of 0.2 to 0.8 bar.

The method may comprise a subsequent step of known specific process intended to make the aqueous albumin solutions suitable to various therapeutic uses in accordance with the European Pharmacopoeia, such as their adjustment to the physiological pH if appropriate, to the isotonicity in the case of an intravenous injection and to a physiologically acceptable salt concentration, and/or conditioning, for example in freeze-dried or liquid form.

The invention also relates to a virally safe aqueous albumin solution obtainable by implementing the method of the invention, in which the transport and binding sites of therapeutically active ingredients are available in the albumin. This albumin solution is further characterised in that it is free from macromolecules having a sedimentation constant, according to Svedberg Ph. et al. ("Ultracentrifüg", 7th edition, Ed. Steinkopff, Dresden, 1940) above 7 S (i.e. a molecular weight of about 160 kDa). In particular, this albumin solution contains at most 1% albumin polymers with a size smaller than 100 nm, preferably smaller than 20 nm.

The invention further relates to an albumin composition for therapeutic use obtained by processing said albumin solution according to the invention to make it suitable to a clinical use.

The safety achieved with these albumin compositions for therapeutic use makes it possible to suppress the pasteurisation step, a source of drawbacks as mentioned above, and therefore, to add usual protection stabilisers against thermal effects, which also bind on the albumin sites, thus preventing albumin from binding the relevant molecules. The albumin of these compositions according to the invention retains its binding and transport potential of various active ingredients, and through this binding, reduces their toxicity or increases the bioavailability by a depot effect.

One can also mention other applications in which the albumin compositions according to the invention may be used:
- stabilisation against denaturation and oxidation of proteins in low concentrations (lower than 1 g/L) and with high specific activities, such as factor VIII, the von Willebrand factor and their recombinant equivalents, specific immunoglobulins, monoclonal antibodies, vaccines (viral, bacterial, proteinic, DNA vaccines), allergens for the detection of allergies in sensitive patients, cytokines or peptidic hormones;
- excipient for proliferation and incubation media for in-vitro fertilisation of human oocytes; and
- control standard proteins acting as placebos in clinical studies.

BRIEF DESCRIPTION OF DRAWINGS

The invention will become more apparent upon review of the following examples, with reference to the accompanying drawings in which.

EXAMPLE 1

Figure 1:
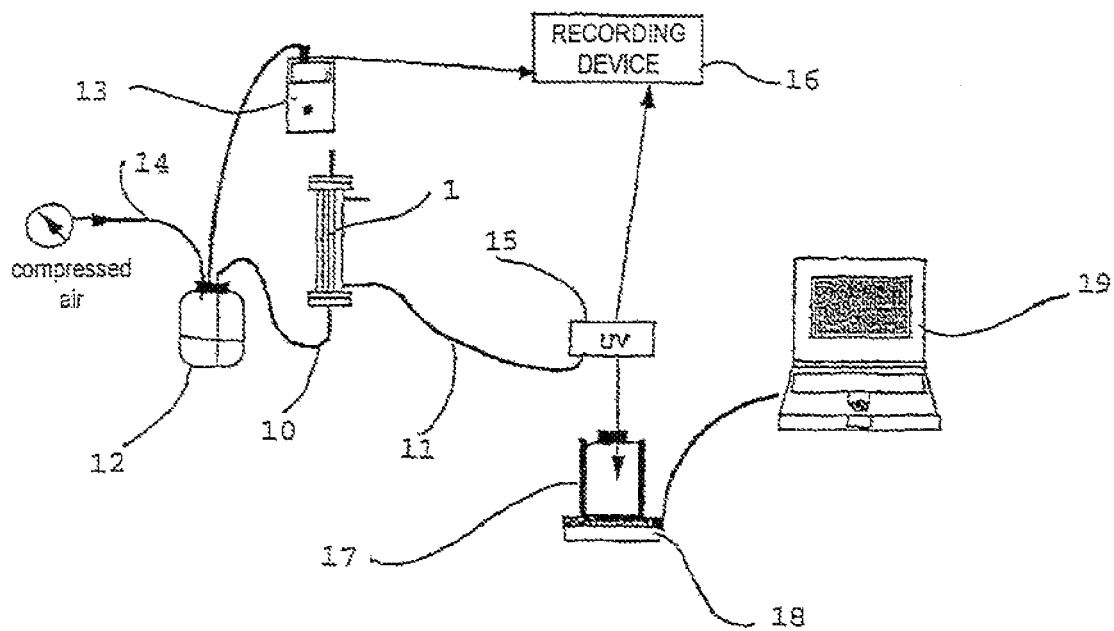
FIG. 1 shows a device for implementing the method of the invention.

1.1 Methodology For Implementing the Nanofiltration Method (FIG. 1)

A filtration device 1 containing a PLANOVA® 15-nm filter with a surface area of 0.01 m² (from Asahi, Japan) is equipped with tubes 10, 11 at the retentate (pre-filtration solution) outlet and at the filtrate (post-filtration solution) inlet and outlet, made of pharmaceutically compatible materials, with diameters of about 5 mm, closed by clamps. The device is arranged on a stand (not shown) in vertical position with the help of graspers.

The inlet of the 15-nm filter is connected, through the tube 10, to a pressure vessel 12 the pressure of which is measured with a digital pressure gauge 13 connected to the upstream filter circuit.

Before use, an integrity test is carried out on the 15-nm filter in accordance with the manufacturer's procedure: "Air leakage test during the integrity pre- and post-filtration test of PLANOVA® 15, 35, 75-nm filters".

Then, the system is rinsed. For that purpose, the compressed air inlet 14 is connected to the pressure vessel 12 filled with a volume of about 100 ml NaCl at 9 g/L. The flask is pressurised progressively until a pressure of 0.5 bar is reached at the inlet of the 15-nm filter. The 15-nm filter is filled while air is released at the retentate outlet, without filling the outside of the filter fibres. The lower outlet is open and connected to an optical density measurement detection cell 15 connected to a recording device 16, the top filtrate outlet remaining clamped. The rinse filtrate is collected in a container 17 on a weighing scale 18 connected to and controlled by a microcomputer 19 that records the filtrate weight increase, which makes it possible to monitor the instantaneous filtration flow rate. The necessary time to filter a minimum volume of 40 mL at 0.5 bar is measured, and the average flow rate in mL/min is deduced. The system is progressively depressurised and all the outlets are clamped. Depending on the temperature required for the nanofiltration, the system can be at room temperature (about 20° C.) or placed in an oven in which the working temperature is between 25 and 60° C.

1.2 Albumin Solutions

As reference aqueous albumin solutions, solutions at 20 g/L, pH 7, containing 9 g/L NaCl are used. The albumin starting material used, noted A, except for Examples 6 and 9 below, is the one obtained by fractionation of human plasma according to Kistler et al. and having undergone alcohol elimination process, diafiltration and concentration by ultrafiltration. It should be noted that the above fractionation of various sources of plasma generally results in albumin with variable characteristics due to the biological nature of the starting material. This albumin may therefore influence the duration of the nanofiltration, the yield, etc.

Albumin aqueous solutions to be filtered are prepared from the reference solutions above, by modification of characteristics thereof such as concentration, pH and ionic strength. Their volumes are adjusted so as to provide the desired protein loads. Depending on the particular example, the albumin concentrations vary from 15 g/L to 80 g/L. The pH is adjusted by adding 0.5 M NaOH or HCl and the ionic strength is adjusted by adding sodium chloride. Then, the albumin solutions are all prefiltered on commercially available 0.2-μm filters.

1.3 Nanofiltration of an Albumin Solution

Once the filtration of a predetermined volume of albumin is achieved, the filter inlet is closed. For rinsing, one volume of purified water for injection (PWI) is introduced into the repressurised vessel 12, and the filter is flushed out. The filtrate is collected until a perceptible reduction in optical density which is monitored on the recording device 16. The downstream circuit is then flushed out to collect the finished filtrate. Samples are taken from the filtrate and submitted to subsequent analytic tests such as polymer assays, virus titrations, etc. The duration of filtration of one volume of albumin solution required to provide a fixed protein load is also measured, and the filtration yield is determined as the quotient between the albumin amount contained in the filtrate and in the retentate.

After use, an integrity test is carried out on the 15-mm filter in accordance with the manufacturer's procedure: "Air leakage test during the integrity pre- and post-filtration test of PLANOVA® 15, 35, 75-nm filters".

EXAMPLE 2

Two preliminary tests are carried out to assess the feasibility of the nanofiltration in terms of protein load, duration and yield, when the nanofiltration is implemented with albumin solutions A (Example 1) filtered at 20° C. and under 0.5-bar pressure. Volumes of
solutions A are prepared with protein loads of 0.5 kg/m$^2$ and 1 kg/m$^2$. The results are shown in Table 1.

TABLE 1

| Solutions | Protein load (kg/m$^2$) | Filtration duration (min.) | Protein recovery (%) |
|---|---|---|---|
| A | 0.5 | 190 | 98 |
| A | 1 | 282 | 99 |

The above results show that, depending on the selected conditions, the nanofiltration of albumin solutions A provides a protein load of 1 kg/m$^2$ without filter clogging and with an excellent yield. It also appears that doubling the protein load does not result in a nanofiltration duration twice as long.

The results of the tests have therefore prompted the Applicant to consider the nanofiltration of albumin solutions with a view to provide higher protein loads, while optimising some influencing parameters if needed.

EXAMPLE 3

Figure 2:
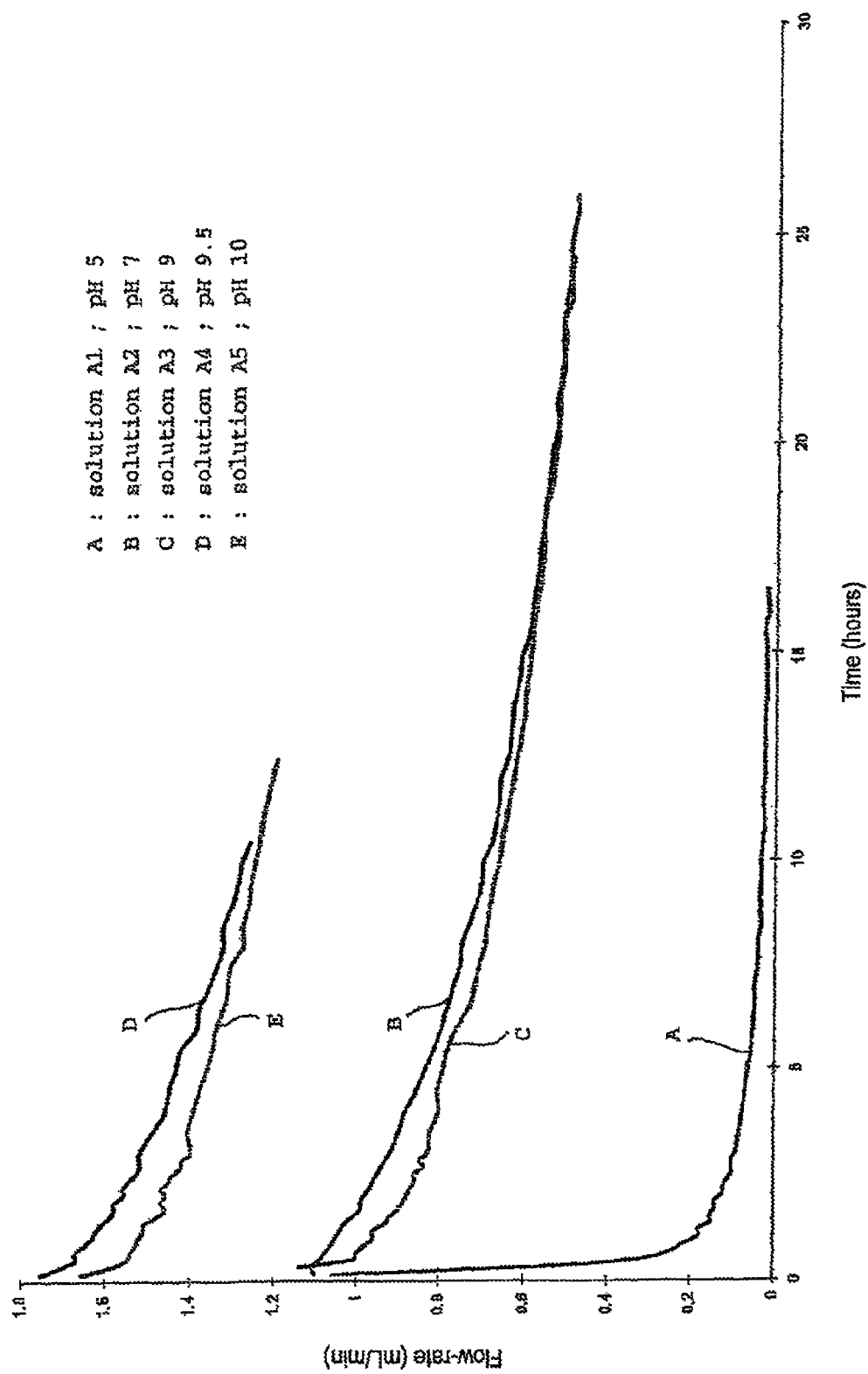
FIGS. 2 to 6 are plots showing the variations of the instantaneous filtration flow rate (mL/min) versus the nanofiltration duration, obtained on the basis of various parameters.

The dependence of the filtration durations and yields to the pH of the albumin solutions in a such a way as a protein load of 4 kg/m$^2$ is provided is determined using a batch of albumin A as starting material. Five solutions of albumin at 40 g/L, A1 to A5, are prepared in a solution of NaCl at 9 g/L, and adjusted to pH 5, 7, 9, 9.5 and 10 respectively, with 0.5 M solutions of HCl or NaOH, and submitted to a nanofiltration. The nanofiltration tests are carried out at 20° C. at a pressure of 0.5 bar. FIG. 2 shows the plots of filtration flow rate (mL/min) versus nanofiltration duration for each of the solutions considered.

An analysis of these plots shows, with solution A1 (pH 5), a rapid reduction in flow rate and, as a consequence, filter clogging. With solutions A2 and A3, there is a reduction in the initial flow rate which is faster with solution A3, but with quite acceptable variations, no filter clogging being observed after more than 25 hours of filtration. The best results are obtained with solutions A4 and A5, i.e. at pH 9.5 and 10, with higher respective initial flow rates and shorter filtration durations than with solutions A2 and A3, solution A4 showing the most optimal initial flow rate.

EXAMPLE 4

Figure 3:
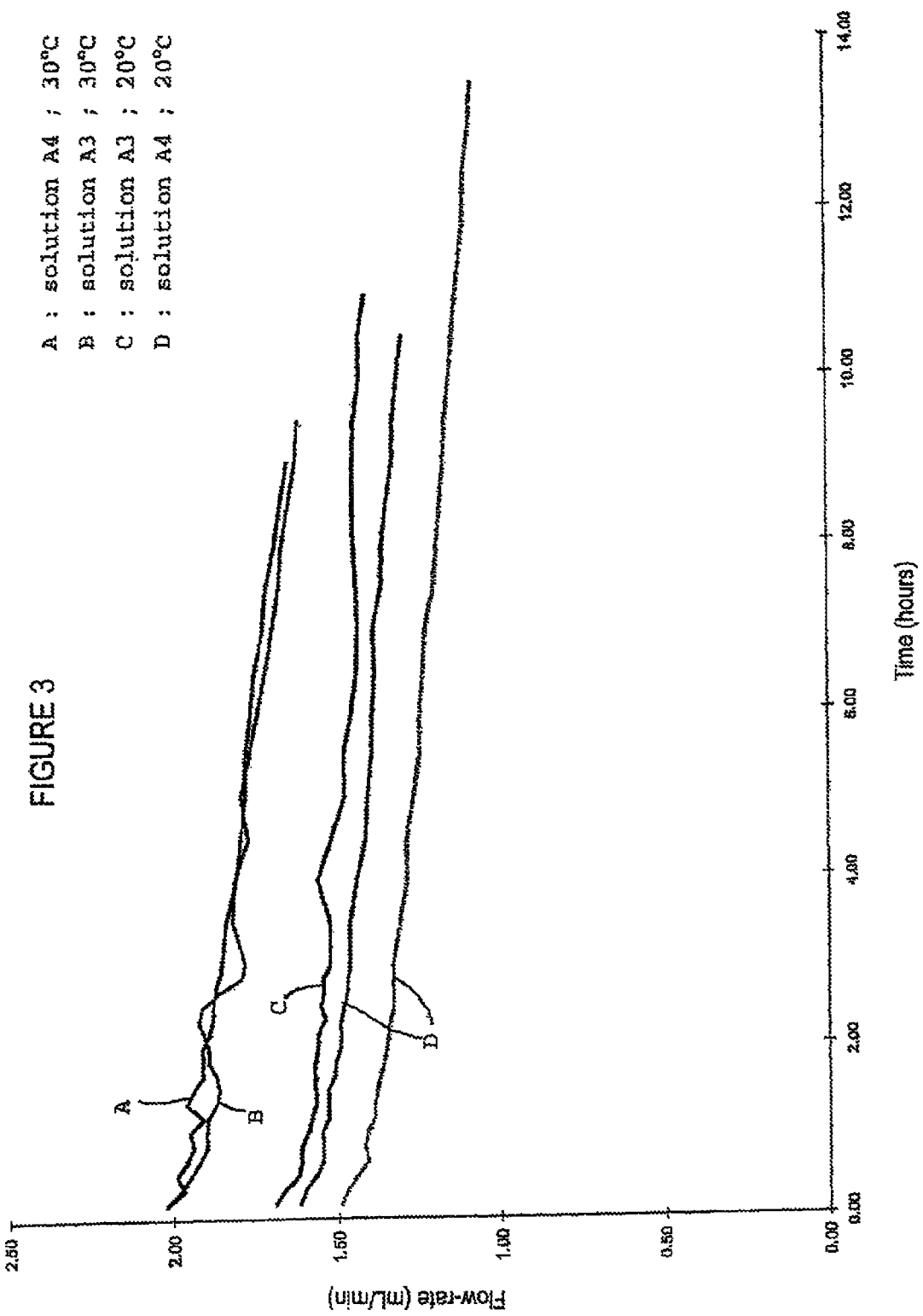

In this example, the joint effect of pH and temperature which provides a protein load of 4 kg/m$^2$ is tested on solutions A3 and A4, defined in Example 3, at 20° C. and 30° C. The nanofiltration tests are carried out at a pressure of 0.5 bar. The filtration durations thus obtained are listed in Table 2. FIG. 3 compiles the plots of filtration flow rate (mL/min) versus nanofiltration duration for each of the solutions considered.

TABLE 2

| Solutions | Temperature (° C.) | Filtration duration (h) | Yield (%) |
|---|---|---|---|
| A3 | 20 | 11 | 98 |
| A3 | 30 | 9.5 | 98 |
| A4* | 20 | 12.75 ± 0.75 | 98 |
| A4 | 30 | 9 | 98 |

*Two nanofiltration tests

The shortest filtration durations are observed at 30° C. with almost super imposable flow rate plots (solutions A3 and A4) without any progressive filter clogging. At 20° C., the filtration flow rates are slightly lower than at 30° C.

EXAMPLE 5

Figure 4:
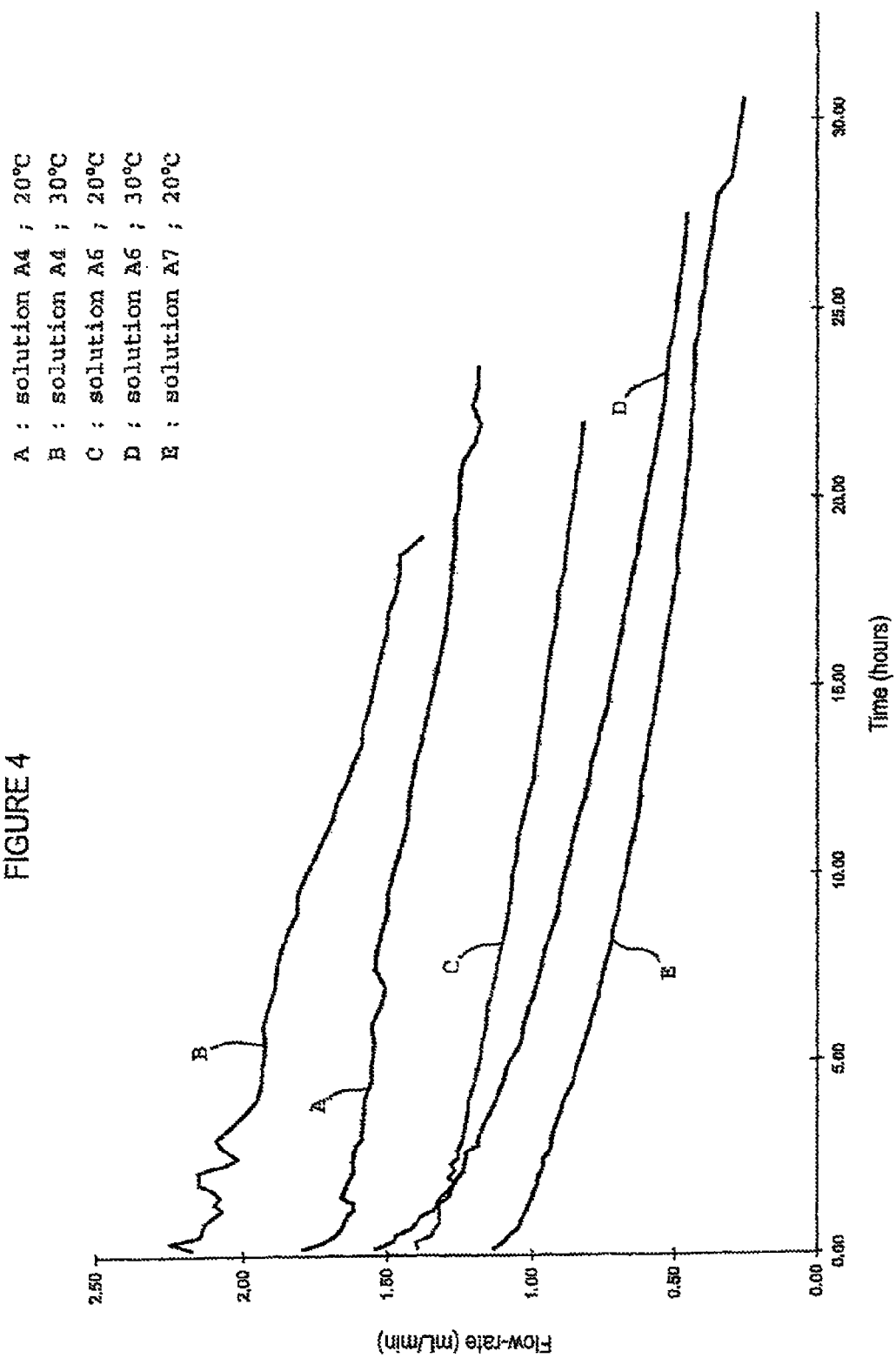

This example is intended to show the joint influence of albumin concentration and temperature on nanofiltration in such a way as a protein load of 8 kg/m$^2$ is provided, by analysing the filtration durations obtained (Table 3) and the flow rate plots (FIG. 4). In this series of tests, solutions A4 (40 g/L), A6 (60 g/L) and A7 (80 g/L) are used, all of them containing 9 g/L NaCl, pH 9.5, and being submitted to a nanofiltration at a pressure of 0.5 bar.

TABLE 3

| Solutions | Temperature (° C.) | Filtration duration (h) | Yield (%) |
|---|---|---|---|
| A4 | 20 | 24.6 | 98 |
| A4 | 30 | 19.5 | 98 |
| A6 | 20 | 22.5 | 98 |
| A6 | 30 | 28.4 | 98 |
| A7 | 20 | 31 | 98 |

An analysis of the results from Table 3 and FIG. 4 shows that the filter can bear a load of 8 kg/m$^2$ without any clogging. In particular, optimal filtration conditions are obtained with solution A4 at 30°0 C. With solution A6, the initial filtration flow rate is higher at 30° C. than at 20° C. with, in addition, a longer filtration duration. These results have therefore prompted the Applicant to consider a nanofiltration temperature of 20° C. for the most concentrated solution A7. Under these conditions, the filtration duration is the longest duration observed and the initial flow rate is the lowest flow rate observed.

EXAMPLE 6

Figure 5:
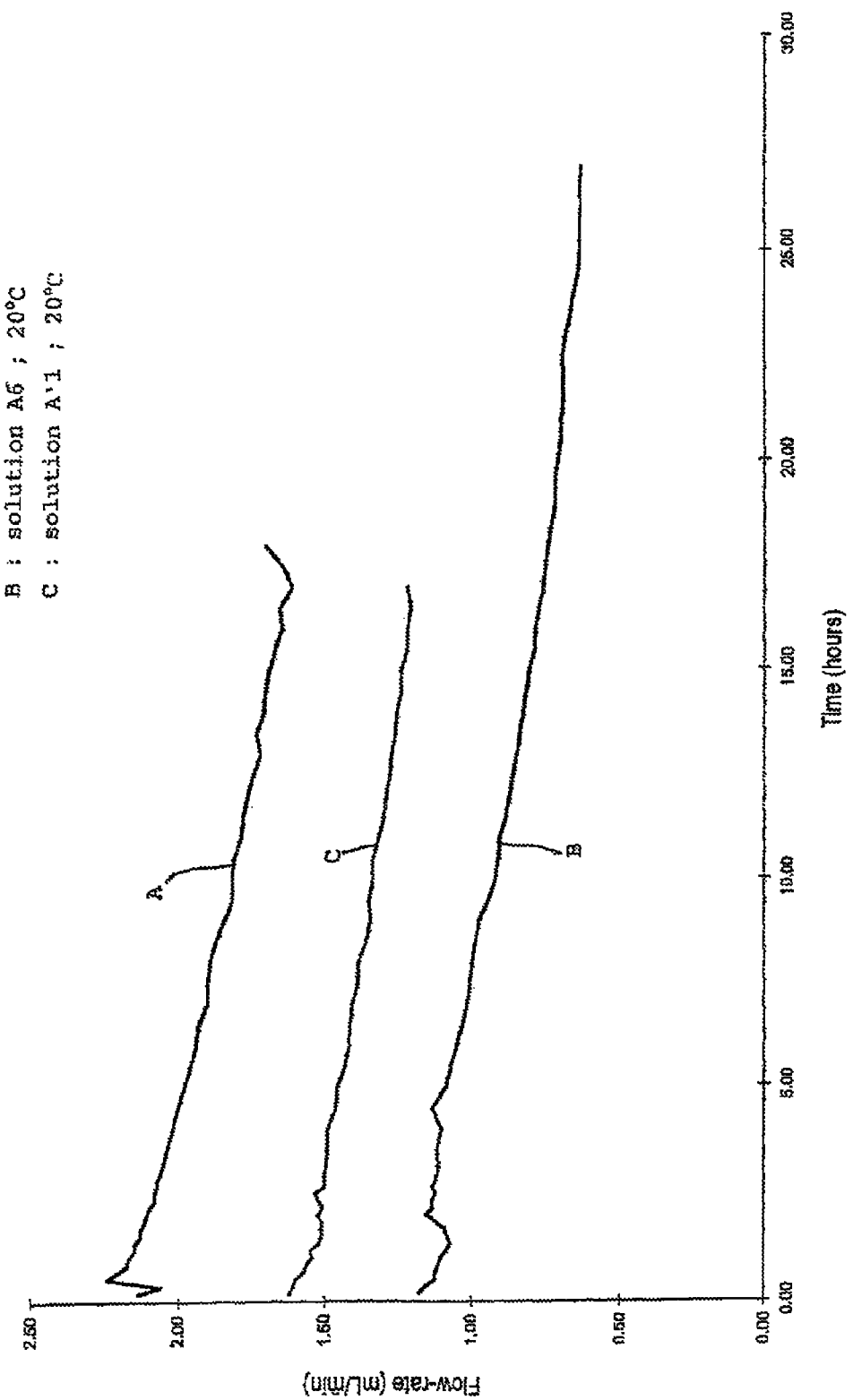

Three nanofiltration tests are carried out with solutions prepared from two different albumin starting materials. The first starting material is albumin A and the second one is albumin A purified by column ion-exchange chromatography (named A'). In this series of tests, solutions A4 and A6 from Example 5, and a solution A'1 (60 g/L, NaCl at 9 g/L, pH of 9.5), which are then submitted to a nanofiltration at 20 and 30° C. at a pressure of 0.5 bar, are used in order to provide a protein load of 8 kg/m². Table 4 shows the filtration durations and yields. FIG. 5 shows the plots of filtration flow rate (mL/min) versus nanofiltration duration for each of the solutions considered.

TABLE 4

| Solutions | Temperature (° C.) | Filtration duration (min) | Yield (%) |
|---|---|---|---|
| A4 | 30 | 18.5 | 98 |
| A6 | 20 | 27.5 | 98 |
| A'1 | 20 | 17 | 98 |

The shortest nanofiltration duration is that observed with A'1. However, the most optimal initial flow rate Is observed with solution A4.

EXAMPLE 7

The effect of a variation in ionic strength in the albumin solutions on the filtration durations and yields is studied with three albumin solutions A at 40 g/L, prepared in purified water for injection (solution A8), in a NaCl solution at 9 g/L (solution A2; ionic strength: 0.15) and in a NaCl solution at 30 g/L (solution A9; ionic strength: 0.5), respectively, all three being at pH 7. The nanofiltration tests are carried out at 20° C. at a pressure of 0.5 bar so as to provide a constant protein load of 4 kg/m². The results are compiled in Table 5.

TABLE 5

| Solutions | Concentration of NaCl (g/L) | Filtration duration (h) | Yield (%) |
|---|---|---|---|
| A8 | 0 | 24.5 | 98 |
| A2 | 9 | 18.7 | 98 |
| A9 | 30 | 22 | 98 |

Figure 6:
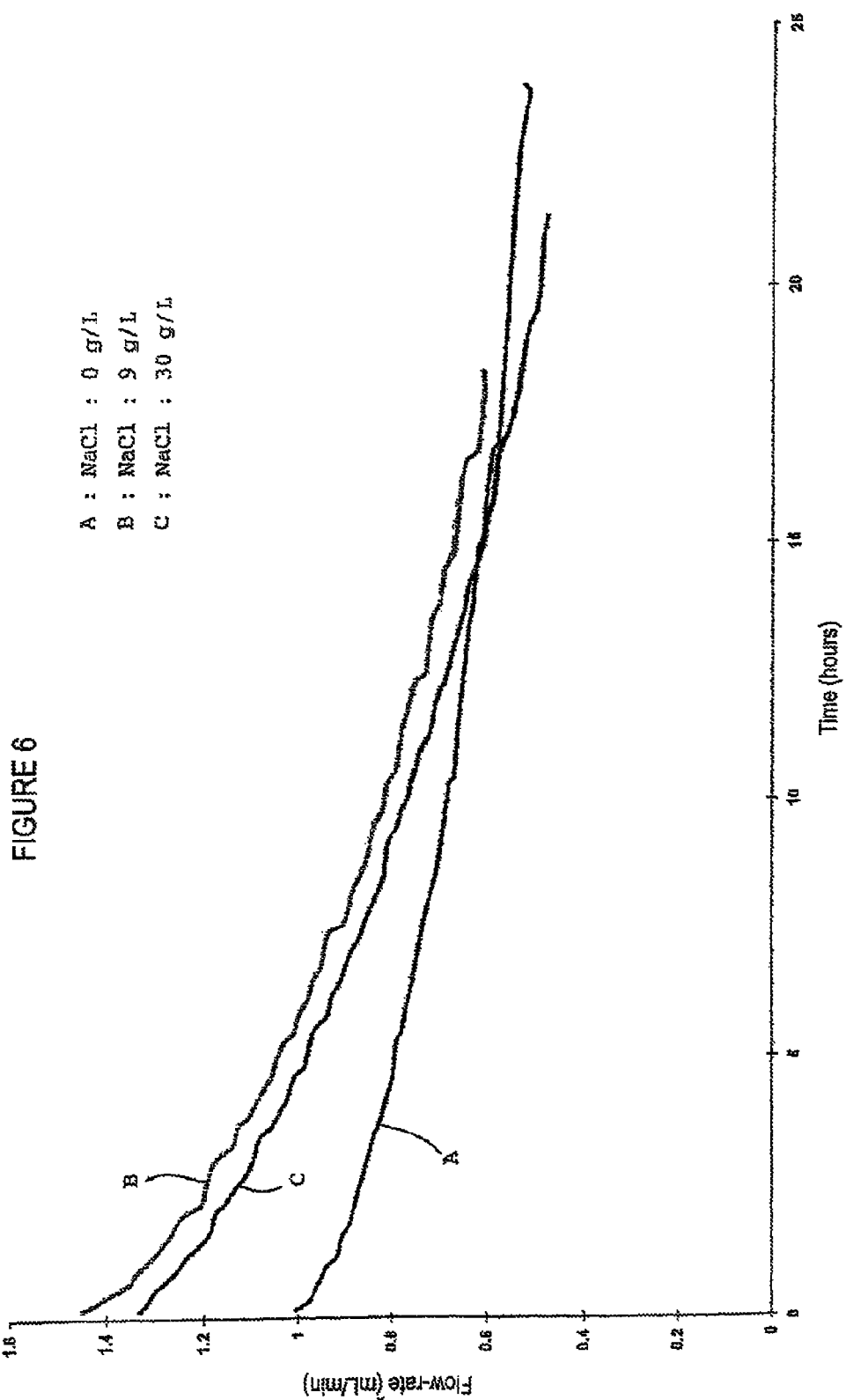

The best result, in terms of optimised filtration duration and yield, is obtained with an ionic strength of 0.15, close to that corresponding to isotonicity. This result is confirmed by monitoring the filtrate weight increase, which makes it possible to plot the variations in the filtration flow rate (mL/min) versus the nanofiltration duration for the studied solutions (FIG. 6). In this example, it appears that increasing the NaCl concentration to 30 g/L does not reduce the filtration duration.

EXAMPLE 8

This example is intended to demonstrate the influence of variations in protein load and nanofiltration pressure on the filtration durations and yields in the products obtained. For that purpose, two solutions of albumins A (Example 2) and A2 (pH 7) are used. The results are shown in Table 6.

TABLE 6

| Solutions | Protein load (kg/m²) | Pressure (bar) | Filtration duration (min) | Yield (%) |
|---|---|---|---|---|
| A2 | 2 | 0.5 | 355 | 100 |
| A | 2 | 0.8 | 457 | 98 |
| A2 | 4 | 0.5 | 1 350 | 98 |
| A2 | 4 | 0.8 | 1 730 | 98 |

These results demonstrate that, with solutions A and A2, a pressure increase gives longer filtration durations in spite of the fact that solution A is less concentrated than solution A2. The results obtained with solutions A2 show that the PLANOVA® 15-nm filters have a protein load or capacity of 4 kg/m² and that a pressure increase does not decrease the filtration duration.

EXAMPLE 9

This example is intended to demonstrate the possibility of implementing nanofiltration on an industrial scale by using PLANOVA® 15-nm filters with surface areas of 1 m². The albumin used is obtained by fractionation according to the method of Kistler et al. and is made therapeutically active by heating at 60° C. for 10 hours in the presence of a suitable stabiliser, in accordance with the requirements of the European Pharmacopoeia. The albumin B thus obtained is then mixed with a buffer comprising: 0.01 M trisodium citrate, 0.12 M glycine, 0.016 M L-Lysine, 0.001 M calcium chloride and 0.17 M sodium chloride, pH 7-7.5. The final concentration of the albumin solutions is 20 g/L. After being prefiltered on 0.2-μm filters, various solutions thus obtained are submitted to a nanofiltration as described in Example 1, at room temperature and at a pressure of 0.5 bar. The volumes of solution B percolating through the filter are determined so as to provide a protein load of 120 g/m². The same nanofiltration tests are carried out using filters of 0.01 m². Table 7 compiles the results of filtration durations and yields obtained with both filters, as average values of 3 tests.

TABLE 7

| Solutions B | Filtration duration (h) | Yield (%) |
|---|---|---|
| Filter of 0.01 m² | 3.1 ± 0.1 | 87 ± 4 |
| Filter of 1 m² | 2.5 ± 0.1 | 83 ± 1 |

The results obtained show that using filters with surface areas of 1 m² results in a shorter filtration duration compared to that obtained with filters having surface areas of 0.01 m², but with a very slight decrease in filtration yield.

EXAMPLE 10

The same solutions B and working conditions as in Example 9 are used to measure the reduction in polymer content after nanofiltration (Table 8).

TABLE 8

| Solutions B | Polymer content before filtration (%) | Polymer content after filtration (%) |
|---|---|---|
| Filter of 0.01 m² | 3.1 | 0.47 ± 0.13 |
| Filter of 1 m² | 4.3 ± 0.7 | 0.38 ± 0.05 |

It should be noted that the pasteurisation of albumin gives polymers in a percentage that, however, always remains lower than the 5% limit recommended by the European Pharmacopoeia (4th edition, chapter "solution of human albumin", page 642). The nanofiltration tests carried out on the two filters surfaces considered provide an approximately 10-fold reduction in polymer content in both cases.

EXAMPLE 11

To show the influence of variations in the working conditions of the nanofiltration (filter surface area, pressure and temperature) and of the physicochemical parameters of the albumin solutions (pH, buffer composition), on the rate of viral reduction, viruses are introduced into different solutions of albumin A (20 g/L) which are submitted to nanofiltration tests. The tests are carried out by infecting the albumin solutions with bacteriophage virus Phi-X 174, suspensions of which are obtained in accordance with AFNOR Standard NFT 72-181 (December 1989). This virus is a good marker for the 15-nm filter as its size is between 25 and 30 nm, which corresponds to the non-enveloped viruses that are transmissible to humans, such as parvovirus B19, the inactivation by pasteurisation of which is not satisfactory.

The results obtained are shown in Table 9.

TABLE 9

| Filter surface area (m²) | Pressure (bar) | T (° C.) | Osmolality (mosm) | Buffer composition | pH | Viral reduction (Δ log) |
|---|---|---|---|---|---|---|
| 0.01 | 0.5 | 35 | 280 | NaCl: 0.15M | 7.2 | 5.9 |
| 0.001 | 0.5 | 35 | 280 | NaCl: 0.15M | 7.2 | 6.5 |
| 0.001 | 0.2 | 35 | 280 | NaCl: 0.15M | 7.2 | >5.0 |
| 0.001 | 1.0 | 35 | 280 | NaCl: 0.15M | 7.2 | 4.9 |
| 0.001 | 0.5 | 26 | 280 | NaCl: 0.15M | 7.2 | >5.5 |
| 0.001 | 0.5 | 35 | 280 | NaCl: 0.15M | 4.1 | >6.0 |
| 0.001 | 0.5 | 35 | 555 | NaCl: 0.30M | 7.2 | 4.2 |
| 0.001 | 0.5 | 35 | 610 | NaCl: 0.15M; Sucrose: 100 g/L | 7.2 | >6.3 |
| 0.001 | 0.5 | 35 | 335 | $Na_2SO_4$: 0.15M | 7.2 | 3.7 |
| 0.001 | 0.5 | 35 | 280 | NaCl: 0.15M Tween ® 80: 0.06% | 7.2 | >6.5 |

An analysis of the results shows that, with variations in the working conditions:
  the sole variation in the filter surface area and temperature, whichever albumin solution considered, does not even nearly have an influence on the rate of viral reduction;
  a pressure increase from 0.5 bar to 1.0 bar has an unfavourable influence on the rate of viral reduction which, however, remains high (>4 log).
Variations in the physicochemical parameters of the albumin A solutions show that:
  the presence of a detergent (Tween® 80) and a non-ionic compound (sucrose), and a variation in pH, do not even nearly have an influence on the rate of viral reduction;

on the other hand, replacing NaCl with a divalent salt, sodium sulfate, has a negative influence on this rate which becomes lower than the threshold allowed by the control authorities. The same phenomenon is observed when the NaCl concentration is increased (from 0.15 M to 0.3 M), although the rate of reduction remains satisfactory.

EXAMPLE 12

The properties of albumin A, nanofiltered without any stabiliser, in the transport and binding of medicines, are studied by comparing them with those obtained with two different albumin A batches pasteurised in the presence of sodium caprylate.

For that purpose, three solutions A4 (Example 3) are provided, one of which has been nanofiltered under the conditions of the invention. These solutions are then processed into pharmaceutical formulations in a 0.07 M phosphate buffer, pH 7.4, to give albumin compositions, A'4, A"4 and A'''4, with concentrations of 2.5 g/L. The albumin compositions A"4 and A'''4, not nanofiltered, are pasteurised in the presence of sodium caprylate, respectively. A sample of 1 mL is taken from each of the compositions, and a volume of between 10 μL and 1 000 μL of a parent alcohol-based solution of [$^{14}$C]warfarine and [$^{14}$C]diazepam at 0.1 M respectively, two active ingredients of the respective class of anticoagulants and neurotropes, is added to the albumin compositions considered in order to provide variable concentrations in these active ingredients. The mixture is then homogenised.

The study of the properties of albumin in binding the two above active ingredients is based on the methodology of equilibrium dialysis, known to those skilled in the art, and whose principle is summarised below. A dialysis device including a cell with two compartments separated by a suitable dialysis membrane is obtained. One volume V of an albumin/active ingredient mixture is introduced into compartment 1 and the same volume V of dialysis buffer (phosphate buffer, as defined above) is introduced into compartment 2. Once the equilibrium is reached, after a few hours, compartment 1 contains albumin-bound and unbound active ingredient and compartment 2 contains unbound active ingredient. Some samples are taken from each compartment 1 and 2 and radioactivity is measured by liquid scintillation. These measurements determine the respective concentrations in albumin-bound and unbound active ingredients.

Table 10 gives the percentages of albumin-bound [$^{14}$C] diazepam obtained with compositions A'4, A"4 and A'''4 respectively, in which increasing volumes of active ingredient have been added. Table 11 shows the results obtained with [$^{14}$C]warfarine instead of [$^{14}$C]diazepam. The results are shown as the average value of 5 tests.

TABLE 10

| Albumin compositions | Total concentration in [$^{14}$C]diazepam (μm) | Percentage of albumin-bound [$^{14}$C]diazepam |
|---|---|---|
| A'4 | 1.68 ± 0.06 | 80.9 ± 1.46 |
| | 4.17 ± 0.28 | 82.34 ± 1.92 |
| | 8.04 ± 0.24 | 78.08 ± 1.83 |
| | 40.09 ± 1.28 | 57.18 ± 2.14 |
| | 65.27 ± 3.46 | 48.88 ± 1.49 |
| | 115.02 ± 4.83 | 36.38 ± 1.69 |
| A"4 | 1.09 ± 0.23 | 34.46 ± 2.04 |

TABLE 10-continued

| Albumin compositions | Total concentration in [$^{14}$C]diazepam (μm) | Percentage of albumin-bound [$^{14}$C]diazepam |
|---|---|---|
| | 5.52 ± 0.53 | 32.26 ± 1.34 |
| | 21.95 ± 0.42 | 31.00 ± 0.93 |
| | 42.84 ± 5.67 | 31.85 ± 2.99 |
| | 85.00 ± 13.6 | 30.12 ± 2.00 |
| | 109.79 ± 10.96 | 29.12 ± 2.67 |
| A''' 4 | 1.23 ± 0.09 | 38.47 ± 1.88 |
| | 2.91 ± 0.21 | 40.93 ± 4.83 |
| | 11.55 ± 0.19 | 37.85 ± 1.25 |
| | 44.98 ± 3.14 | 34.96 ± 0.6 |
| | 86.09 ± 5.01 | 33.04 ± 1.17 |
| | 107.9 ± 9.43 | 30.74 ± 1.78 |

The results show that the higher the concentration in [$^{14}$C]diazepam in the albumin composition A'4, the lower the percentage of albumin-bound [$^{14}$C]diazepam. This demonstrates the presence of one saturable site or bond and one non-saturable bond in albumin.

Increasing the concentration in [$^{14}$C]diazepam in the albumin compositions A''4 and A'''4 results in appreciably constant percentages of albumin-bound [$^{14}$C]diazepam. Therefore, the binding site identified in the albumin A, nanofiltered without any stabiliser, in composition A'4 is no more functional since it is occupied by the stabiliser.

TABLE 11

| Albumin compositions | Total concentration of [$^{14}$C]warfarine (μm) | Percentage of albumin-bound [$^{14}$C]warfarine |
|---|---|---|
| A'4 | 1.99 ± 0.19 | 93.32 ± 0.49 |
| | 10.12 ± 0.71 | 91.75 ± 0.75 |
| | 34.29 ± 2.28 | 83.43 ± 1.11 |
| | 62.73 ± 3.55 | 71.74 ± 1.20 |
| | 103.66 ± 4.24 | 55.34 ± 2.94 |
| | 123.43 ± 8.07 | 47.83 ± 2.03 |
| A''4 | 1.71 ± 0.19 | 88.18 ± 0.82 |
| | 8.35 ± 1.13 | 87.61 ± 0.84 |
| | 30.97 ± 2.98 | 81.14 ± 2.07 |
| | 54.40 ± 10.02 | 73.24 ± 3.46 |
| | 102.08 ± 14.70 | 57.02 ± 4.36 |
| | 119.90 ± 6.96 | 53.11 ± 3.46 |
| A''' 4 | 1.69 ± 0.08 | 88.58 ± 0.32 |
| | 8.33 ± 0.30 | 87.66 ± 0.28 |
| | 31.65 ± 0.72 | 80.39 ± 0.89 |
| | 57.17 ± 3.81 | 71.01 ± 1.68 |
| | 104.64 ± 6.28 | 55.04 ± 0.68 |
| | 127.98 ± 4.83 | 49.77 ± 2.66 |

The results from this table show that the percentages of albumin-bound [$^{14}$C]warfarine vary with the increase in [$^{14}$C]warfarine concentration in the three albumin compositions considered. Therefore, the binding site in the albumin is not saturated by the stabiliser.

A comparison of the results shown in Tables 10 and 11 demonstrates that albumin behaves differently in respect of the considered medicines. This may be due to the structures of the medicines considered, compared with the configurations of the albumin binding sites. These studies also determined the various binding constants (Ka) of both medicines on the different albumins A'4, A''4 and A'''4, as shown in Table 12.

TABLE 12

| Albumin composition | Ka [$^{14}$C]diazepam (mM$^{-1}$) | Ka [$^{14}$C]warfarine (mM$^{-1}$) |
|---|---|---|
| A'4 | 187 | 215 |
| A''4 | 4.2 | 135 |
| A''' 4 | 3.35 | 118 |

EXAMPLE 13

The power of the nanofiltered albumin to stabilise von Willebrand factor (vWf) was assessed using dry heating tests of vWf at 80° C. for 72 hours. On the basis of preliminary tests, it was found that adding a mixture of judiciously selected excipients, such as glycine and arginine, to a solution of vWf, provided its stabilisation during the dry heating test (80° C., 72 hours). Although the activity of vWf (vWf:Ag) was retained (>82% compared to the non-heated vWf), its multimeric profile was not maintained, which was revealed by the disappearance of multimers with high molecular weights (>10), responsible for the therapeutic effect of vWf.

To overcome this drawback, three solutions of 1 g/L of vWf were prepared in the presence of glycine and arginine, and of nanofiltered albumin A for therapeutic use. The characteristics of the solutions thus obtained, A10, A11 and A12, are shown in Table 13.

TABLE 13

| Solutions | Albumin (g/L) | Glycine (g/L) | Arginine (g/L) |
|---|---|---|---|
| A10 | 15 | 5 | 40 |
| A11 | 15 | 10 | 40 |
| A12 | 15 | 5 | 30 |

These solutions are then submitted to freeze-drying (45±3 hours) and dry heating as defined above. After heating, the addition of purified water for injection (PWI) to the dry residues reconstitutes solutions A11-A12. The following parameters are analysed: appearance of the solution, dissolution time, activity of vWf and multimeric profile, as measured by electrophoresis. Table 14 shows the results obtained.

TABLE 14

| Solutions | Solution appearance | Dissolution time (min) | vWf:Ag (%)** | Multimeric profile |
|---|---|---|---|---|
| A10 | L* | <1 | 91 | C*** |
| A11 | L* | <1 | 89 | C*** |
| A12 | L* | <1 | 87 | C*** |

*clear, without visible particles
**ratio between the activity of heated vWf and non-heated vWf
***conform to the original product (before heating)

These results demonstrate on the one hand that the presence of albumin does not have any negative effect on the stabilisation by heating of vWf, which is revealed by a clear solution appearance (without visible particles), a very short solubilisation time, and in particular, the preservation of vWf activity, and on the other hand, that this presence also maintains the integrity of its high molecular weight multimers.

The invention claimed is:

1. A method for purifying an albumin solution containing virus particles to produce a virally safe albumin solution comprising a step of submitting an aqueous albumin solution, with a concentration of 15 g/L to 80 g/L, an ionic strength in the range of 0.01 to 0.3M, and a pH not lower than 7, to a nanofiltration carried out on qualified filters having porosities of 15±2 nm to 20 nm±2 nm in a temperature range of 15° C. to 55° C.

2. The method according to claim 1 wherein the pH of the aqueous albumin solution is in the range of 7.8 to 11.5.

3. The method according to claim 1, wherein the ionic strength is provided by the addition of a pharmaceutically acceptable salt of an alkali metal.

4. The method according to claim 3, wherein the salt of an alkali metal is sodium chloride present in an amount imparting to the albumin solution an ionic strength of 0.15 M.

5. The method according to claim 1, wherein the concentration of the aqueous albumin solution is in the range of 40 g/L to 60 g/L.

6. The method according to claim 1, wherein the temperature of the aqueous albumin solution is between 30° C. and 55° C.

7. The method according to claim 1, wherein the nanofiltration of the aqueous albumin solution is carried out in two successive steps on two filters with decreasing porosities, respectively.

8. The method according to claim 7, wherein the two successive nanofiltration steps are carried out on filters with porosities of 23 to 50 nm and 15 or 20 nm, respectively.

9. The method according to claim 1, wherein it is implemented with regenerated cellulose filters of 15 nm having a surface area of 0.01 $m^2$, at a pressure not exceeding 1 bar.

10. The method according to claim 9, wherein the pressure is in the range of 0.2 to 0.8 bar.

11. The method according to claim 1, wherein the albumin is obtained by ethanol extraction and by purification by ion-exchange or affinity chromatography.

12. The method according to claim 1, further comprising a subsequent step of processing the aqueous albumin solution to make it suitable to a therapeutic use.

13. The method according to claim 1, wherein the pH of the aqueous albumin solution is in the range of 9 to 10.5.

* * * * *